(12) United States Patent
Vanegas et al.

(10) Patent No.: US 11,589,749 B2
(45) Date of Patent: Feb. 28, 2023

(54) OPTICALLY MONITORING BRAIN ACTIVITIES USING 3D-AWARE HEAD-PROBE

(71) Applicant: Northeastern University, Boston, MA (US)

(72) Inventors: Morris Dwight Vanegas, Cambridge, MA (US); Qianqian Fang, North Reading, MA (US)

(73) Assignee: Northeastern University, Boston, MA (US)

(*) Notice: Subject to any disclaimer, the term of this patent is extended or adjusted under 35 U.S.C. 154(b) by 571 days.

(21) Appl. No.: 16/519,861

(22) Filed: Jul. 23, 2019

(65) Prior Publication Data

US 2020/0022581 A1 Jan. 23, 2020

Related U.S. Application Data

(60) Provisional application No. 62/863,097, filed on Jun. 18, 2019, provisional application No. 62/701,927, filed on Jul. 23, 2018.

(51) Int. Cl.
*A61B 5/00* (2006.01)
*A61B 5/369* (2021.01)
*A61B 5/1455* (2006.01)

(52) U.S. Cl.
CPC .......... *A61B 5/0073* (2013.01); *A61B 5/0064* (2013.01); *A61B 5/369* (2021.01); *A61B 5/6814* (2013.01); *A61B 5/6843* (2013.01); *A61B 5/14552* (2013.01); *A61B 5/6803* (2013.01); *A61B 2562/0233* (2013.01); *A61B 2562/046* (2013.01)

(58) Field of Classification Search
None
See application file for complete search history.

(56) References Cited

U.S. PATENT DOCUMENTS

| | | | |
|---|---|---|---|
| 9,814,426 B2 * | 11/2017 | Connor | A61B 5/02055 |
| 2009/0270745 A1 * | 10/2009 | Sankai | A61B 5/0261 |
| | | | 600/504 |
| 2018/0239430 A1 * | 8/2018 | Tadi | H01L 33/58 |
| 2019/0380634 A1 * | 12/2019 | Yamada | A61B 5/14552 |

OTHER PUBLICATIONS

Neurolite Advanced Medical Solutions, "NIRS—Near Infrared Spectroscopy", 2019, 2 pages, https://neurolite.ch/en/products/nirs.

(Continued)

*Primary Examiner* — Yi-Shan Yang
(74) *Attorney, Agent, or Firm* — Hamilton, Brook, Smith & Reynolds, P.C.

(57) ABSTRACT

A flexible head probe and modular head probe system that includes an optical functional near-infrared spectroscopy (fNIRS) system and integrated position sensor. The head probe and modular head probe system determines physiological data based upon the optical information gathered by the fNIRS system and gathers motion and position data from the position sensor. The physiological data and motion and position data are combined to permit topographical and tomographic analyses of a user's brain tissue.

18 Claims, 9 Drawing Sheets

(56) References Cited

OTHER PUBLICATIONS

Barker, et al, "Autoregressive model based algorithm for correcting motion and serially correlated errors in fNIRS", Biomedical Optics Express 1366, vol. 4, No. 8, 14 Pages, Aug. 1, 2013.
Boas, et al, "Twenty years of functional near-infrared spectroscopy: introduction for the special issue", NeuroImage vol. 85 (2014) 1-5.
Chitnis, et al, "Functional imaging of the human brain using a modular, fibre-less, high-density diffuse optical tomography system". Biomedical Optics Express 4275, vol. 7, No. 10, 14 Pages, Oct. 1, 2016.
Choi, et al, "Time-Divided Spread-Spectrum Code-Based 400 fW-Detectable Multichannel fNIRS IC for Portable Functional Brain Imaging", IEEE Journal of Solid-State Circuits, vol. 51, No. 2, 484-495, Feb. 2016.
Cox, Robert W., "AFNI: Software for Analysis and Visualization of Functional Magnetic Resonance Neuroimages", Computers and Biomedical Research 29, 162-173 (1996) Article No. 0014.
Dementyev, et al, "SensorTape: Modular and Programmable 3D-Aware Dense Sensor Network on a Tape", UIST 2015 Proceedings of the 28th Annual ACM Symposium on User Interface Software & Technology, 649-658.
Deng, et al, "Characterization of structural-prior guided optical tomography using realistic breast models derived from dual-energy x-ray mammography", Biomedical Optics Express 2366, Jul. 1, 2015, vol. 6, No. 7, 14 Pages.
Fang, et al, "Monte Carlo simulation of photon migration in 3D turbid media accelerated by graphics processing units", Optics Express 20178, Oct. 26, 2009, vol. 17, No. 22, 13 Pages.
Fang, et al, "Tetrahedral Mesh Generation From Volumetric Binary and Gray-Scale Images", 2009, I2009 IEEE International Symposium on Biomedical Imaging: From Nano to Macro, pp. 1142-1145.
Fang, Qianqian, "Mesh-based Monte Carlo method using fast ray-tracing in Plucker coordinates", Biomedical Optics Express 165, Aug. 2, 2010, vol. 1, No. 1, 11 Pages.
Fang, et al, "Compositional-prior-guided image reconstruction algorithm for multi-modality imaging", Biomedical Optics Express 223, Aug. 2, 2010, vol. 1, No. 1, 13 Pages.
Ferrari, et al, A brief review on the history of human functional near-infrared spectroscopy (fNIRS) development and fields of application, NeuroImage vol. 63 (2012) 921-935.
Gowerlabs Ltd., "Lumo fNIRS neuroimaging ecosystem", https://www.gowerlabs.co.uk/lumo, Retrieved on Nov. 9, 2019, 15 Pages.
Hitachi Group, "ETG-4100: Features", https://www.hitachi.com/businesses/healthcare/products-support/opt/etg4100/contents1.html, Retrieved on Nov. 6, 2019, 3 Pages.
Huppert, et al, "Comparison of group-level, source localized activity for simultaneous functional near-infrared spectroscopy magnetoencephalography and simultaneous fNIRS-fMRI during parametric median nerve stimulation", Neurophoton. 4(1), 015001 (2017), 14 Pages.
Krall, et al, "The role of the right temporoparietal junction in attention and social interaction as revealed by ALE meta-analysis", Brain Struct Funct. Mar. 2015 ; 220(2): 587-604.
Lu, et al, "The Narrative Impact of Active Video Games on Physical Activity Among Children: A Feasibility Study" JMed Internet Research, Oct. 2016; 18(10): e272, 17 Pages.
Luhmann, et al, M3BA: A Mobile, Modular, Multimodal Biosignal Acquisition Architecture for Miniaturized EEG-NIRS-Based Hybrid BCI and Monitoring, IEEE Transactions on Biomedical Engineering, vol. 64, No. 6, Jun. 2017, 12 Pages.
Mar, Raymond A., The neuropsychology of narrative: story comprehension, story production and their interrelation Neuropsychologia 42 (2004) 1414-1434.
McConville, et al, "Anthropometric Relationships of Body and Body Segment Moments of Inertia", Air Force Aerospace Medical Research Laboratory, Dec. 1980, 113 Pages.
Moyer, Ilan Ellison, "A Gestalt Framework for Virtual Machine Control of Automated Tools" Massachusetts Institute of Technology, 2013, 153 Pages.
NIRx Medical Technologies, LLC, "NIRScout", https://nirx.net/nirscout, Retrieved on Nov. 6, 2019, 16 Pages.
NIRx Medical Technologies, LLC, "NIRSport", https://nirx.net/nirsport, Retrieved from https://web.archive.org/web/20160616212831/http://nirx.net/nirsport on Nov. 26, 2019, 5 Pages.
Pardo, et al, "The anterior cingulate cortex mediates processing selection in the Stroop attentional conflict paradigm", Proc. Natl. Acad. Sci. USA vol. 87, pp. 256-259, Jan. 1990.
Peek, Nadya, "Making Machines that Make: Object-Oriented Hardware Meets Object-Oriented Software" Massachusetts Institute of Technology, 2016, 150 Pages.
Strangman, et al, "Factors affecting the accuracy of near-infrared spectroscopy concentration calculations for focal changes in oxygenation parameters". NeuroImage vol. 18, No. 1 (2003) 865-879.
Tak, et al, "Statistical analysis of fNIRS data: A comprehensive review", NeuroImage vol. 85 (2014) 72-91.
Tran, et al, "Fast and high-quality tetrahedral mesh generation from neuroanatomical scans", arXiv:1708.08954 [physics,med-ph], 2017, 20 Pages.
Vanegas, et al, "Towards a fiberless, modular, and wearable full-head fNIRS system with built-in 3D self-calibrating orientation sensor network", Oct. 2018, 1 Page.
Vanegas, Morris, "coreyXY", http://morrisvanegas.com/forthem/corexy3.html, 2015, 28 Pages.
Vanegas, et al, "A Mobile Phone Based Reflectance Pulse Oximeter", iBiophotonics Congress: Biomedical Optics Congress 2018, 2 pages.
Wyser, et al, "Wearable and modular functional near-infrared spectroscopy instrument with multidistance measurements at four wavelengths", Neurophotonics 4(4), 041413(2017), 14 Pages.
Yao, et al, "A Rapid Approach to Build Jacobians for Optical Tomography via Monte Carlo Method and Photon "Replay "", Optics in the Life Sciences 2017, 3 Pages.
Atsumori, et al, "Development of wearable optical topography system for mapping the prefrontal cortex activation", Review of Scientific Instruments 80, 043704 (2009), 7 Pages.
Yuan, et al, "Denoising in Monte Carlo Photon Transport Simulations Using GPU-accelerated Adaptive Non-Local Mean Filter", Biophotonics Congress: Biomedical Optics Congress 2018.
Yucel, et al, "Reducing motion artifacts for long-term clinical NIRS monitoring using collodionfixed prism-based optical fibers". NeuroImage 85 (2014) 192-201.
Zhao, etc al, "Review of recent progress toward a fiberless, whole-scalp diffuse optical tomography system", Neurophoton 5(1), 011012 (2017), 12 Pages.
Zimmermann, et al, "Detection of motor execution using a hybrid fNIRS-biosignal BCI: a feasibility study", Journal of NeuroEngineering and Rehabilitation 2013, 15 Pages.
NIRx Medical Technologies, LLC, "NIRSport2", https://nirx.net/nirsport, Retrieved on Nov. 6, 2019, 20 pages.

* cited by examiner

OPTICALLY MONITORING BRAIN ACTIVITIES USING 3D-AWARE HEAD-PROBE

RELATED APPLICATION(S)

This application claims the benefit of U.S. Provisional Application No. 62/701,927 filed on Jul. 23, 2018 and U.S. Provisional Application No. 62/863,097 filed on Jun. 18, 2019. The entire teachings of the above applications are incorporated herein by reference.

GOVERNMENT SUPPORT

This invention was made with government support under Grant Number EB026998 awarded by the National Institutes of Health. The government has certain rights in the invention.

BACKGROUND

Functional near-infrared spectroscopy (fNIRS) is a non-invasive technique that utilizes non-ionizing near-infrared (NIR) light to determine the physiological data of a user's head and brain. FNIRS is known as a safe, non-invasive, information-rich, and potentially low-cost neuroimaging method, measuring hemodynamic changes of oxy-hemoglobin ($HbO_2$) and deoxy-hemoglobin (HbR) due to brain activities. Although fNIRS has seen an increase in use, bulky fiber-based connections, cart-sized optical instruments for high-density probes, and lengthy positioning and setup time of prior art devices remain major obstacles for translating fNIRS measurements outside of research environments. In addition, tomography-based fNIRS image reconstructions are known to provide more accurate quantification and localization of brain activations but require accurate measurements of 3-D source/detector positions. In prior art methods, this has been achieved using either a co-registered structural MRI scan—which is often not accessible in many studies—or a separate 3D position tracking system such as a Polhemus scanner. Such external 3D tracking systems can be expensive, require extra training and maintenance as well as additional registration steps. A more portable fNIRS system design is crucial to advance fNIRS outside of laboratory settings.

Several key challenges remain such as a lack of non-invasive continuous monitoring, limited spatiotemporal resolution in in-vivo imaging of human brain dynamics, and required immobility during acquisition. Specifically, a need exists for a fNIRS head-probe design, featuring 1) an integrated position sensor network that automatically obtains 3D position and motion data to enable tomographic fNIRS reconstructions and high image accuracy, 2) ultra-compact lightweight flexible-circuit based head probe modules that can be easily integrated with head wear, 3) inter-connecting multiple flexible head probe modules capable of covering a range of brain regions, including full-head probe system, and 4) high reconfigurability.

SUMMARY

The invention includes a head probe that has a flexible base able to conform to a user's head surface, a first light source, on the surface of the base facing the user's head surface, that propagates light through a user's head tissue, and a first photodetector, on the surface of the base facing the user's head surface, that detects light from the first light source after the light traverses the user's head tissue.

The base may be diamond shaped, composed of two identical triangles connected along one edge. In alternative embodiments the base may be square shaped or triangle shaped. The head probe may also include a position sensor such as an inertial measurement unit that gathers positioning and motion data. The position sensor may include a 3-axis accelerometer and a gyroscope chip. The light propagated may be near infrared light with a wavelength between 600-2500 nm (nanometers). The head probe may also comprise a wireless communication device such as a Bluetooth transceiver.

The head probe may have a communication port configured to temporarily interface with another probe to create an interconnected system. The connected probe may be identical to the head probe or have a different configuration. The first photodetector can detect light from a light source on a connected probe after the light traverses the user's head tissue.

The head probe may also have a second photodetector, on the surface of the base facing the user's head surface, located further from the first light source than the first photodetector. The second photodetector detects light from the first light source after the light traverses the user's head tissue. In such embodiments, the head probe may also have a second light source, on the surface of the base facing the user's head surface, that propagates light through the user's head tissue and the first and second photodetectors can detect light emitted by both the first and second light source after the light traverses the user's head tissue.

A modular head probe system of plural flexible modules. Each flexible module comprising a communication port configured to temporarily interface with another of the plural modules to create an inter-connected system of modules, a light source, on the surface of the module facing the user's head, that propagates light through a user's head tissue, a light detector, on the module facing the user's head, that detects light propagated through a user's head tissue, and a position sensor that gathers motion and positioning data of the module. The modular head probe system also includes a control unit configured to determine physiological data of the user's head tissue based upon the light detected by the photodetectors of the plural flexible modules. The physiological data may be hemodynamics. The physiological data may be determined and motion and positioning data gathered in real time during extended user activity. The control unit is further configured to use the motion and positioning data gathered by the position sensors of the plural modules to recover the locations and spatial arrangements of the light detectors and light sources of the plural flexible modules.

The plural flexible modules, of the head probe system, may be configured to be connected, disconnected, and reconnected in multiple layout configurations. In some embodiments the plural modules are configured to be connected using inter-integrated circuit protocol. The plural modules may be diamond shaped, composed of two identical triangles connected along one edge.

The control unit, of the head probe system, may be configured to use the locations and spatial arrangements of the light detectors and light sources of the plural flexible modules to perform at least one of the following: data cleaning, data processing, data correction, data pruning, and detection of data artifacts on the physiological data. The control unit may include a Bluetooth transreceiver and an external power source connection.

The modular head probe system may further comprise a backend computer configured to determine all possible connection routes between the plural flexible models and control unit and further configured to determine an optimized module layout. The optimized module layout may be defined as maximizing the gestalt ratio. In alternative embodiments, the optimized module layout may be defined as maximizing the average brain sensitivity.

The modular head probe system may further comprise a computer configured to use the locations and the spatial arrangements of the light detectors and the light sources of the plural flexible modules to map the physiological data to a tomographic reconstruction of the user's head tissue.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

The teachings of all patents, published applications and references cited herein are incorporated by reference in their entirety.

Conventional prior art neuroimaging modalities, such as functional MRI (fMRI), Magnetoencephalogram (MEG), and Positron Emission Tomography (PET), have poor portability, making it impossible to continuously measure brain activities in a natural living environment. This invention includes wearable, modular, wireless, and fiber-less functional near-infrared (fNIRS) brain imaging head probe modules and a head probe system comprised of the head probe modules, that proves safe and non-invasively monitoring of brain functions using only low-power light.

FNIRS measures changes in hemoglobin during brain activation to determine brain activity. Hemoglobin, deoxygenated-hemoglobin, and other objects of interest have a different absorption spectrum and absorption coefficients than the tissue, skin and bone that compose a user's head. Therefore, wavelengths of light can be identified that will pass through most of a user's head except for hemoglobin, deoxygenated-hemoglobin, and other objects of interest. The light can be near infrared light in the spectrum of approximate 600-2500 nm. When a light source is placed on a user's scalp so that it emits light through a user's head. Then the light is detected, by a light detector placed on the user's scalp, after it has traversed through the user's head. The behavior of hemoglobin and deoxygenated-hemoglobin over time (hemodynamic responses) can be determined based on the measured magnitude and wavelength of the detected light. Brain activity can then be determined based on hemodynamic responses associated with neuron behavior.

A fNIRS system includes at least one set of optodes, specifically a light source and a light detector, and other electronic or optical components. Light propagates from the light source through the head, scatters, and is detected as it exits the user's head by the light detector. The light source may be a dual wavelength LED source that emits light with wavelengths 690 and 830 nm. The light detector may be photodetector such as a silicon photodiode with an analog-to-digital converter and an integration amplifier. The light source and light detector may be any components capable of emitting and detecting near infrared light respectively. A light source-detector pair forms a path for light called a channel, and the channel separation is the distance between the source and detector. As channel separation is increased, the penetration depth, into the user's head, of the detected light is increased. If the channel separation is too small, the light will only travel through the superficial layer of a user's head. If the channel separation is too large, not enough photons will be able to be detected by the detector at the end of the channel. Ideally, a channel will have a channel separation large enough to allow the light to penetrate to the brain tissue without losing too much light before it is detected by a light detector. This may be a channel separation of up to 40 mm.

Figure 1:
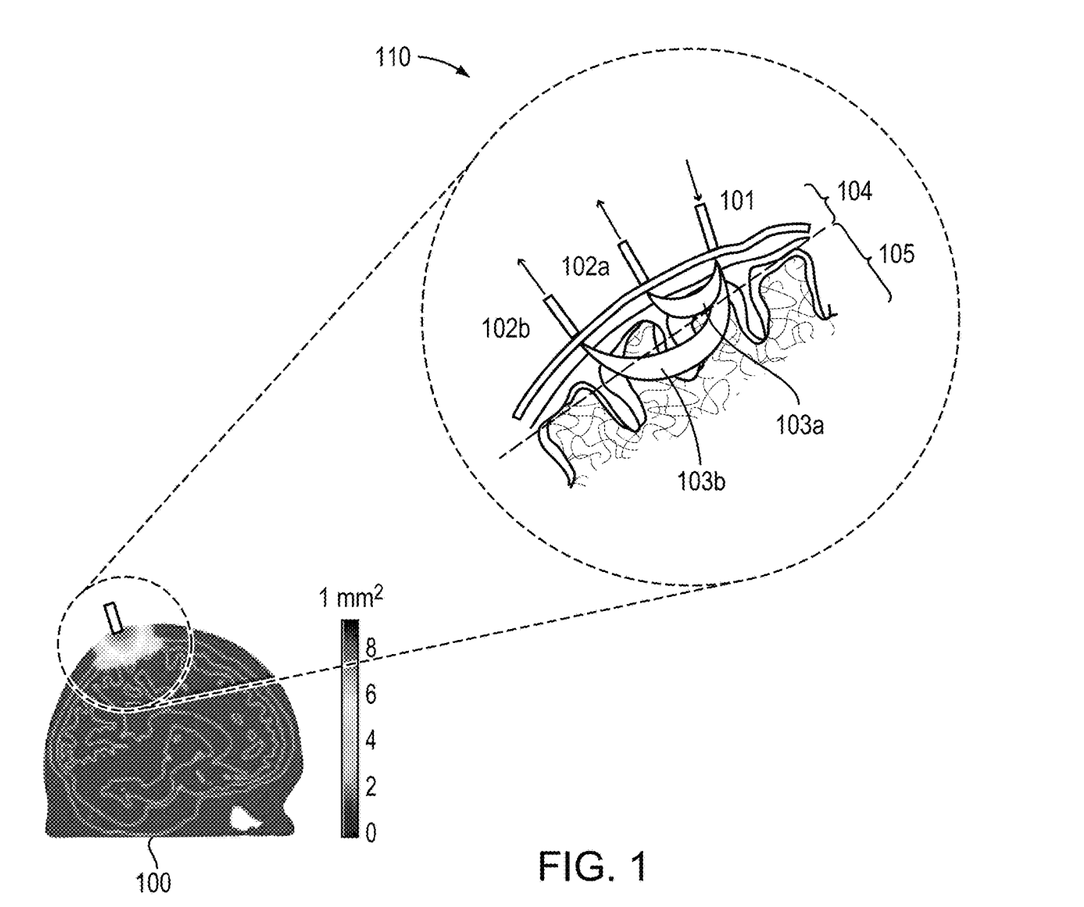
FIG. 1 is a diagram of functional near-infrared spectroscopy with two channels.

FIG. 1 is a diagram of functional near-infrared spectroscopy (fNIRS) system with two channels. A user's head 100, shown in more detail in excerpt 110, includes superficial layer 104 and brain tissue 105. To best determine brain activity, light must penetrate superficial layer 104 and the hemodynamics of brain tissue 105 must be monitored. Light source 101, is placed on a user's scalp and emits light through the user's head. This light is detected by light detectors 102a and 102b. Light source 101 is paired with light detectors 102a and 102b and forms channels 103a and 103b respectively. Light detector 102b, because it has more channel separation, detects light that travels deeper into user's head 100 then light detector 102a. Therefore, light detected at detector 102b that has travelled channel 103b provides data that is correlated with brain tissue 105 hemodynamics, physiological data, and brain activity.

For channels with shorter channel separation, such as channel 103a, the photons emitted by light source 101 have a low probability to pass through the brain tissue 105 and the ability to determine brain activity is limited. However, shorter channels can be used to establish the hemodynamics and other physiological data of superficial layer 104 and that information can be used to normalize data for deeper brain tissue 105 gathered from channels with longer channel separation such as channel 103b. Data from the shorter channel 103a can be used to remove systematic signal contamination from the superficial layer 104 from data from the longer channel 103b via regression. Therefore, it is often desired to have at least two channels with variable channel separation to measure different areas of a user's head. Furthermore, it is beneficial to know, and monitor, the channel separation between a light source 101 and light detectors 102 because the channel separation determines which region of a user's head the detected light has traveled through and provides information regarding. Knowing the channel separation allows for higher accuracy in translating the optical data gathered by light detectors 102 into brain activity. Furthermore, if channel separation changes during user activity that information can be used to perform data cleaning, data processing, data correction, data pruning, and detection of data artifacts on the data gathered by the optodes.

Figure 2A:
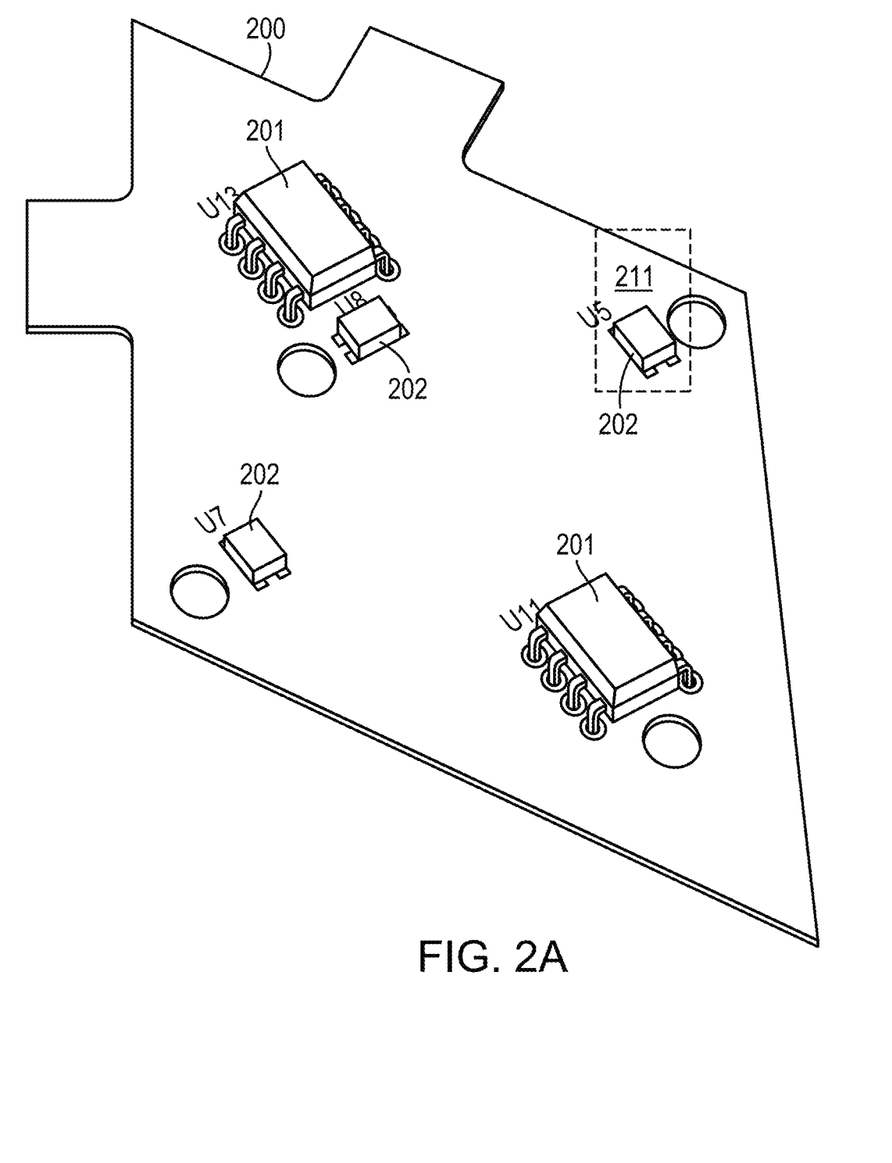
FIG. 2a is a schematic of the side of a head probe module to be placed against a user's head, according to an embodiment of the invention.

FIG. 2a is a schematic of the side of a head probe module to be placed against a user's head, according to an embodiment of the invention. The head probe module shown in FIG. 2a can operate individually as a full head probe. Alternatively, the head probe module can be part of a head probe system comprised of multiple modular head probe modules. The side of the head probe that is placed against a user's head's surface includes a set of optodes for fNIRS. Base 200 is composed of a flexible circuit board capable of conforming to a user's head. Base 200 can support circuit components on both sides while remaining flexible, lightweight, and ultra-compact. Base 200 can be integrated with head wear. Base 200 may be diamond shaped composed of two triangles connected on one side. Alternatively, base 200 may be composed of a single triangle. Base 200 can be any geometric shape based upon the desired area of coverage and head probe module design needs. The head probe module includes three light sources 202 located on base 200. Alternative embodiments may have any number of light sources. The Light sources 202 may be a 640 nm LED (APT2012SECK), a 940 nm LED (APT2012F3C), or another source of near infrared light. The wavelengths of light sources 202 may be between 600-2500 nm and have wavelengths chosen to minimize the potential for hemoglobin cross-talk. When base 200 is placed against a user's head, light sources 202 emit light that propagate through and scatters within the user's head. The head probe module includes two light detectors 201 located on base 200. Alternative embodiments may have any number of light detectors 201. The light detectors 201 may be photodetectors such as silicon photodiodes that include an analog-to-digital converter (ADC), and an integration amplifier. The light detectors 201 detect the light emitted by light sources 202 after the light has traversed a user's head. The amount of light absorbed and the spectrum of light absorbed provides physiological data on the region of the user's head the light traveled through. The physiological data can be hemodynamics that are correlated with brain activity. The light detectors 201 and light sources 202 can form optode pairs and channels to perform fNIRS imaging.

The locations of light detectors 201 and light sources 202 can be chosen to optimize channel separation for fNIRS imaging and to ensure that the light penetrates to the desired regions of a user's head before being detected. The locations of light detectors 201 and light sources 202 can be chosen can be chosen to provide a varied channel separation for fNIRS imaging to allow for normalization of brain tissue data gathered by channels with large channel separation by applying superficial layer data gathered by channels with short channel separation. Large channel separation may be approximately 35 mm between the light source and light detectors. Short channel separation may be approximately 5 mm between the light source and light detectors.

To achieve robust light coupling to the skin and minimize the impact of hair and motion, short tubular light guides (approximately 5 mm) with hemisphere ends may be used couple the end of optodes, such as light detectors 201 and light sources 202, to the scalp of a user. Light guides can be glued directly onto the optodes and encapsulated with a thin layer of flexible black silicone rubber on the side of the base 200 facing the user's head. The black silicone minimizes reflection, protects the electronics from direct skin contact, and acts as a comfort layer for long-term wear. An example short tubular light guide 211 is shown coupled to one of the light sources 202. Prior art, fiber-based fNIRS probes exert large relative motion due to the weight and tethering of the optical fibers. The invention is less sensitive to motion given its compactness and untethered features. Therefore, it can be integrated into pressure-fit headgear and held to the scalp of a user by enclosing it under an elastic cap (such as an electroencephalography-cap). If necessary, collodion, a clinical adhesive, can also be applied to fix the head probe to the skin ether on base 200 or guides 211.

The head probe module embodiment shown in FIG. 2a has three light sources 202 and two light detectors 201 that can form six pairs of optodes and therefore six channels for fNIRS imaging. The embodiment of FIG. 2a includes an optode pair with short channel distance (approximately 8 mm) that provides ability to remove systematic signal contamination from the superficial layer of a user's head via regression and/or data normalization. Furthermore, the embodiment shown in FIG. 2a includes an optode pair with a long channel distance (approximately 40 mm) that provides the maximum penetration into a user's head to monitor brain tissue. Alternative embodiments may have any desired combination of optode pair channel distance. Each optode, light sources 202 and light detectors 201, also have the ability to form a fNIRS pair with an optode located on another head probe module base 200. A pair of optodes located on different modules forms a cross-channel. The ability to create cross channels allows for an increased amount of physiological data that to be gathered. Cross channels also increase the variety of possible channel separation distances allowing for more areas of the user's head to be monitored.

Figure 2B:
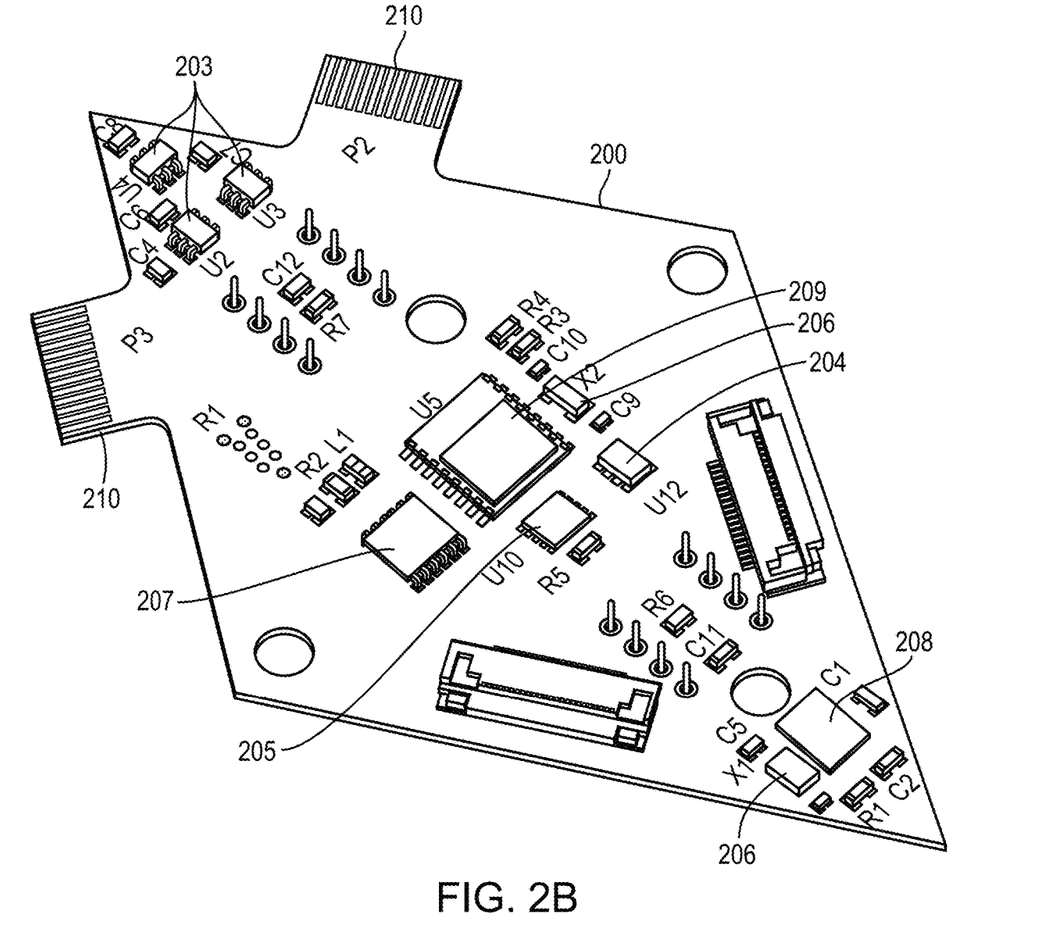
FIG. 2b is a schematic of the side of a head probe module not facing a user's head, according to an embodiment of the invention.

FIG. 2b is a schematic of the side of a head probe not facing a user's head, according to an embodiment of the invention. The side not facing the user's head, contains the components for logic control, data processing, and other non-optical functions. The side not facing the user's head, can include, voltage regulators 203, digital to analog converter 204, current regulator 205, crystals 206, analog multiplexer 207, position sensor 208, and a microcontroller 209. The side not facing the user's head, may also include programming pins. Microcontroller 209 may include a Bluetooth transceiver or other wireless communication device. The position sensor 208 may be an inertial measurement unit 3-axis accelerometer and gyroscope chip with an integrated motion processor to output quaternions. The position sensor 208 may also measure orientation. The position sensor 208 can obtain the 3D positions of the head probe module without the need for external devices. The position sensor 208 can obtain position and motion data for each pair of optodes 201 and 202. Other embodiments of the invention may include any number position sensors and any known type of position sensor used to gather similar data. The position sensors of a head probe system comprised of head probe modules can form an integrated position sensor network that automatically obtains 3D position and motion data. The position sensor network of a head probe system can automatically gather and track the position of optode pairs from different head probe modules that form cross channels.

The head probe module shown in FIGS. 2a and 2b includes communication ports (connection lines) 210. These communication ports 210 can be used to interface with additional head probe modules to create an interconnected head probe system. The communication ports can be located on any amount of the edges of base 200. The communication ports may be dedicated input and output ports that contain four lines needed for inter-integrated circuit ($I^2C$) and one line needed for peer-to-peer (P2P) communication between modules. Communication ports on other edges can be used as complimentary connections. The communication ports form temporary connections, therefore, any number of head probe modules can be connected, disconnected and reconnected, in any configuration, to form any desired shape. The head probe modules may be manufactured as a single connected piece and cut and into individual modules to be rearranged in different configurations. The ability to form temporary connections allows for multiple head probe modules to be connected, disconnected, and reconnected in multiple layout configurations depending upon the region of interest that needs to be covered and other variables.

Once head probe modules are connected, cross channels can be formed between pairs of optodes 201 and 202 located on different bases 200 of the head probe modules that form the head probe system. One embodiment is a group of six head probe modules connected in a straight line, enough to cover the forehead of a user with a single strip. However, any number of head probe modules can be connected into single- or branching chains to form arbitrarily complex head-probe system configurations for different applications. The head probe system can cover a wide range of brain regions by simply disconnecting and reconnecting repeating head probe modules. This modular functionality significantly reduces the design and manufacturing costs as well as the flexibility to accommodate a wide range of brain imaging tasks and different brain region of interest.

One module of the head probe system may be a master module. Master modules can have a side facing the user's head, with a serial-to-USB converter, a Bluetooth transceiver, and an external power source connection instead of the optodes shown in FIG. 2a. An off-the-shelf Bluetooth (RN42, Microchip) transceiver can be used to minimize interference concerns for wireless communication. The system of head probe modules can be connected to the master module using a 5-pin fine-pitch flexible printed circuit (FPC) connector or other connection interface. The master module can send data to a computer for data visualization, as well as distributes power to all head probe modules.

Figure 3:
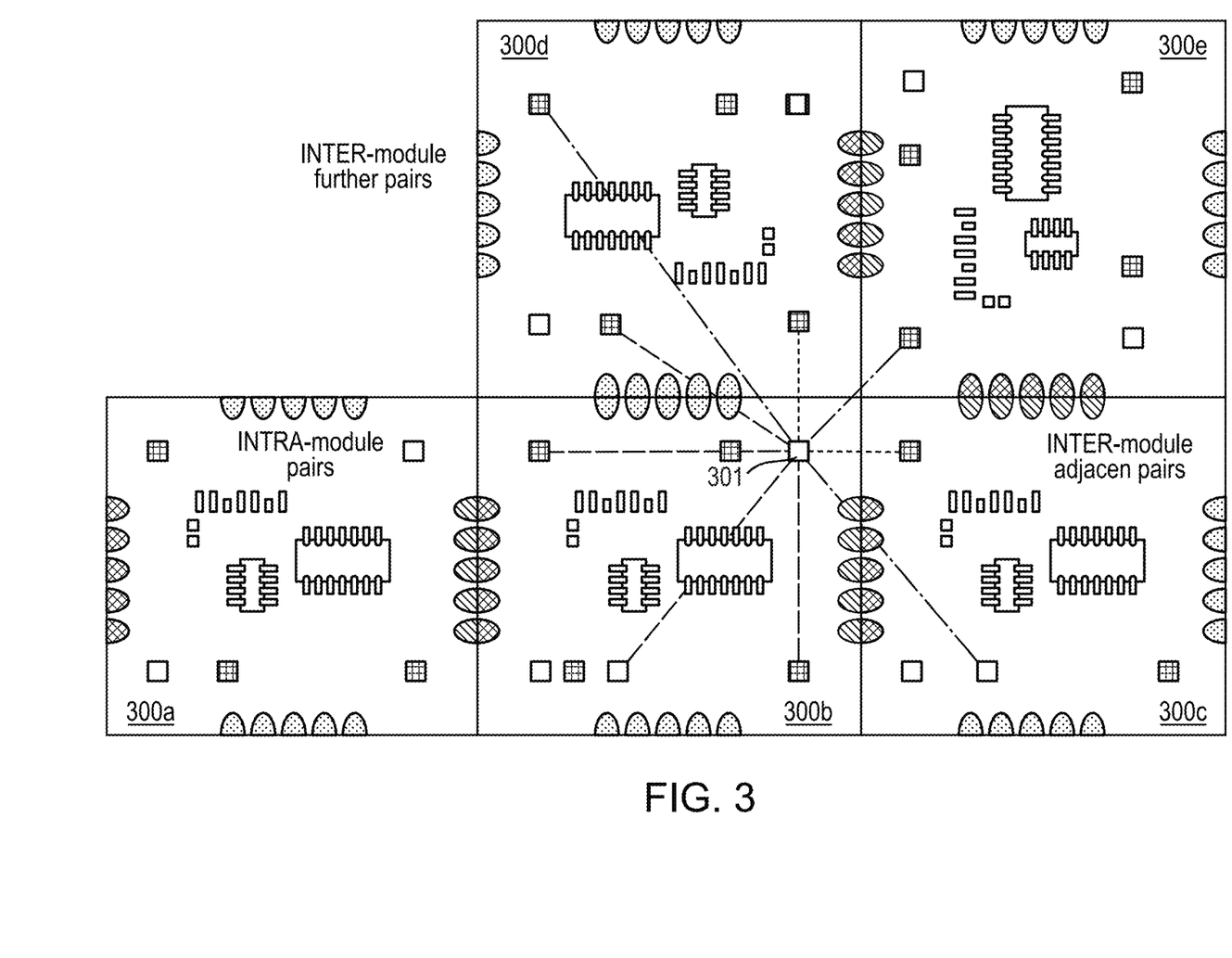
FIG. 3 is an example embodiment of an interconnected head probe system comprised of five head probe modules.

FIG. 3 is an example embodiment of an interconnected head probe system comprised of five head probe modules. Head probe system 300 is comprised of five square head probe modules 300a, 300b, 300c, 300d, and 300e. The number of channels able to be created is illustrated by identified light source 301. Light source 301 can form an optode pair and channel with any light detector on any head probe module 300a, 300b, 300c, 300d, and 300e of head probe system 300. Identified by lines are Intra-module (dashed), inter-module with adjacent neighbors (dotted), and inter-module with further neighbor (dash-dot) channels shown for a single source 301. Any number of head probe modules can be connected into single- or branching chains to form arbitrarily complex head-probe system configurations for different applications or regions of interest. Multiple source-detector channel separation distances can be formed from a single detector by creating optode pairs with light sources on adjacent head probe modules. A head probe module not only provides short- and long-separation measurements between the onboard light sensor sources and light detectors (dashed lines), but also is capable of detecting signals from the sources in adjacent head probe modules (dotted lines). Adjacent head probe modules can be either directly connected to a head probe module or share a side with the sampling detector's head probe module and be indirectly connected through another head probe. Each light detector can also sample further pairs on adjacent and non-adjacent modules (dash-dotted lines). The 3D configuration of the head probe system is determined by the connection topology of the head probe modules (to know if the chain branches, makes a left or right turn, or continues in a straight chain) and the relative position between head probe modules can be measured by position sensors on the modules. The relative orientation between head probe modules may also be measured. Additionally, the fixed geodesic distance between modules allows for accurate position estimation and channel separation distance measurement between all possible source-detector pairs and channels. Head probe modules 300a, 300b, 300c, 300d, and 300e of head probe system 300 can include position sensors to track the location of the modules and automatically determine the distance between optodes and channel separation.

Individual head probe modules or a full head probe system can be embedded under existing headwear without major modifications for continual monitoring during various applications that require physical movements. Additionally, embedding this design into existing headwear minimizes cost, but also permits a user to quickly attach and detach the system. Head probe modules can use Velcro to attach to the inside of headwear, allowing for the ability to remove, re-align, and reconfigure the modules for increased comfort. Head probe modules can be configured for full head coverage or can be placed to increase channel density over a particular region.

The optimal configuration to cover a region of interest with the head probe modules can be determined through an algorithm used to tessellate and interconnect user-specified head probe modules. The configuration can include a determination of the optimal shape of base 200 of the head probe modules and the way to connect the individual head probe modules to form the head probe system. The algorithm starts by covering the region of interest using specified head probe module shapes/dimensions, and automatically determining routes between all modules; from all possible connection routes. An optimized module layout is can be defined by finding the path that traverses all nodes and has the highest gestalt ratio, which is defined as the total number of channels (intra- and inter-) divided by the number of intra-module channels. An optimized module layout can also be defined by finding the path that traverses all nodes and has the highest brain sensitivity. Brian sensitivity is defined as, for a particular channel, how sensitive a measurement at the detector is to changes in the brain tissue. Additionally, other fNIRS related metrics including total counts of intra- and inter-module source-detector pairs, and channel separation distributions can be derived to assess the efficacy of the head probe system. The algorithm may receive user-defined parameters describing the modular system including at least one of, maximum optode separation, head probe module optode layout, region of interest size, shape of the head probe modules, and other variables. Based upon the user-defined parameters, the algorithm can then tessellate the head probe module over the region of interest and determine the optimal connection path for the tessellated head probe modules to form a head probe system.

Figure 4:
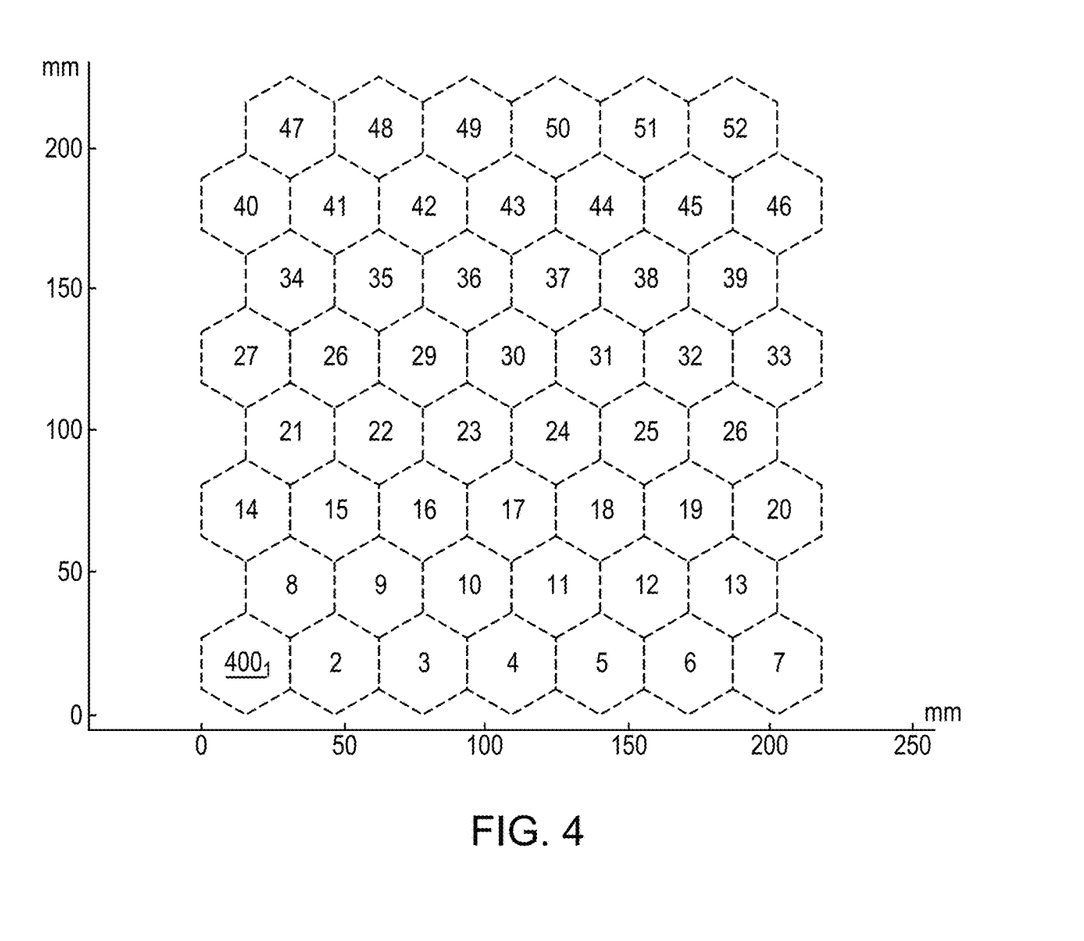
FIG. 4 is a diagram of a head probe shape tessellated over an area.

FIG. 4 is an example of a potential head probe shape tessellated over an area. Potential head probe 400 is shaped as a hexagon. Head probe 400 is tessellated to cover a 200 square millimeter region of interest. After the region of interest is covered, the best way to connect the head probes can be determined.

Figure 5:
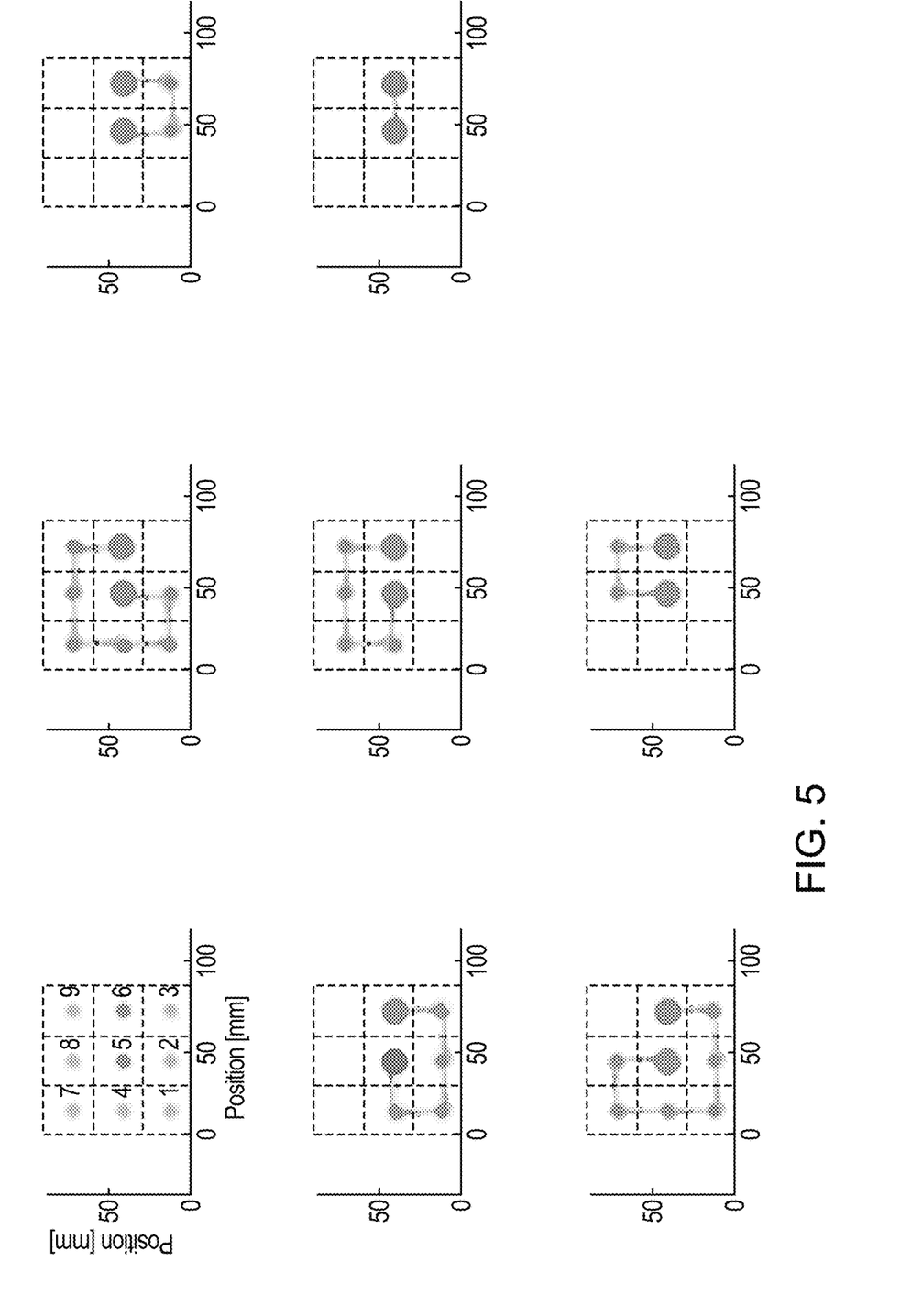
FIG. 5 is an example of the determination of the potential paths for a head probe system comprised of nine square head probe modules.

FIG. 5 is an example of the determination of the potential paths for a head probe system comprised of nine square head probe modules. All possible paths, including incomplete, paths, are identified. A path can only pass through each head probe module once and each module is assumed to have a single input and a single output. However, the input and outputs can be located on any side of the head probe module. For the head probe system comprised of nine square head probe modules shown in FIG. 5 there are 644 total potential paths and 40 potential full paths. After the full paths are identified, the optimal path can be identified.

Figure 6:
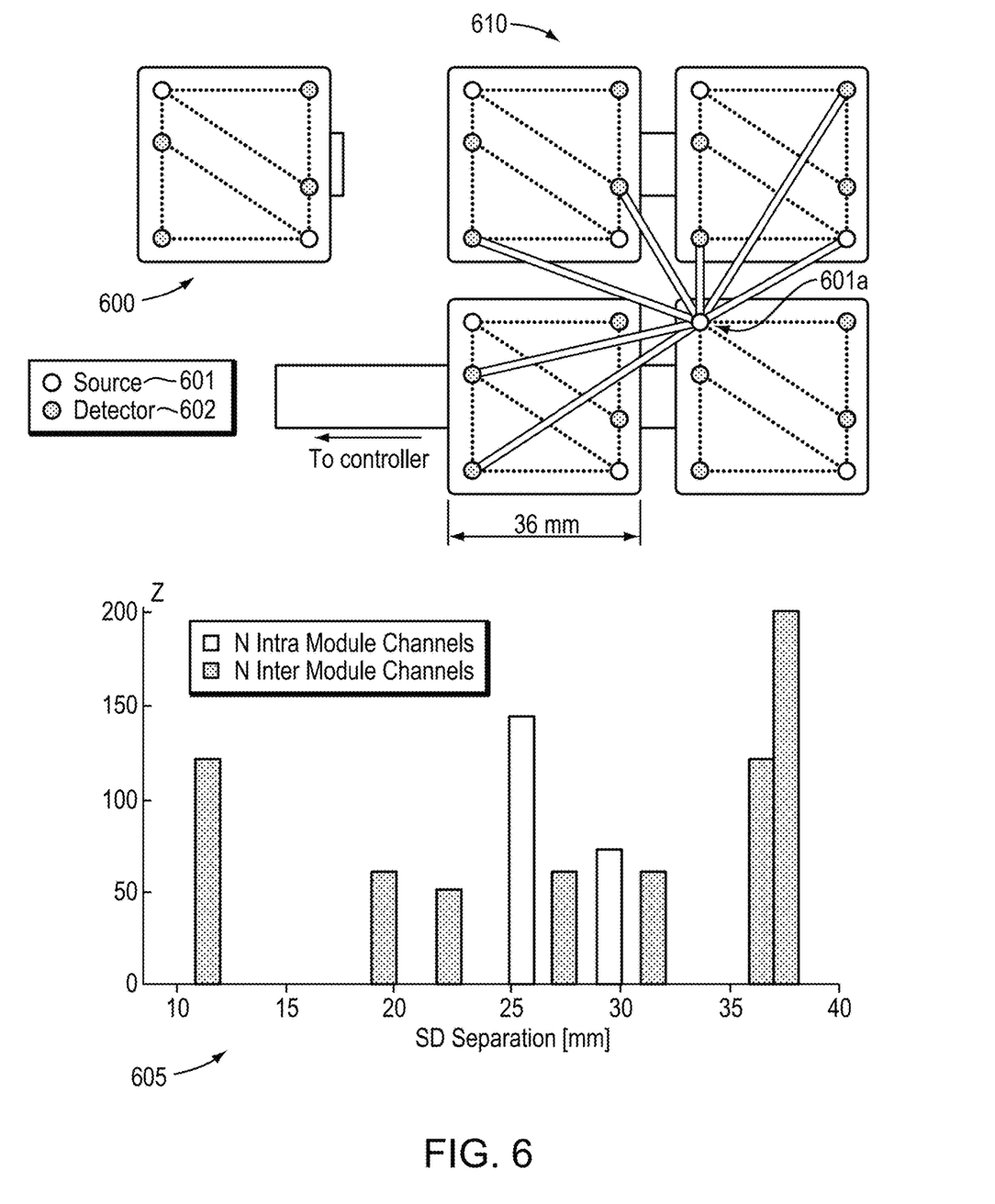
FIG. 6 is an example of determining cross-channels and gestalt ratio for a head probe system of four square head probe modules, according to an embodiment of the invention.

FIG. 6 is an example of determining cross-channels and gestalt ratio for a head probe system of four square head probe modules. The head probe system shown in FIG. 6 is composed of square head probe modules 600. Head probe modules 600 have two light sources 601 and four light detectors 602. The head probe modules have a side length of 36 mm. Head probe modules 600 have the inter-module channels identified by dotted lines connecting the light sources 601 with light detectors 602. Each head probe modules 600 forms eight inter-module channels of varying channel separation. Head probe system 610 is composed of four square head probe modules 600. Head probe system 610 can also have a master module (not shown in FIG. 6). The potential cross channels for a single light source 601a are shown by solid lines connecting light source 601a to light detectors 602. Cross channels with channel separation over a set threshold are not considered because the signal would be too weak to provide useable data. In some embodiments that threshold is set to 40 mm. All of the inter module cross channels and intra module channels are identified for a potential configuration as shown in graph 605. The channel separation for each channel can also be calculated. Graph 605 shows the number of channels and cross channels at each channel separation. The channel separation can be used to determine the brain sensitivity for each channel. After all the channels are identified the average brain sensitivity for each configuration of head probe system 610 can be determined. The gestalt ratio, which is defined as the total number of channels (intra- and inter-) divided by the number of intra-module channels can also be determined and used to identify the optimal configuration. Additionally, other fNIRS related metrics including total counts of intra- and inter-module source-detector pairs, channel separation distributions, and average brain sensitivity can be derived to assess the efficacy of the head probe system configuration. The optimal configuration can be determined based upon the gestalt ratio or other metrics such as average brain sensitivity. While FIG. 6 only shows square head probe modules with a set light source and light detector layout, the gestalt ratio and other metrics can be calculated for any shape and size head probe module and any head probe module layout. Furthermore, different shapes, sizes and layouts can be compared against each other in a specific region of interest or area to discover the optimal configuration.

Figure 7:
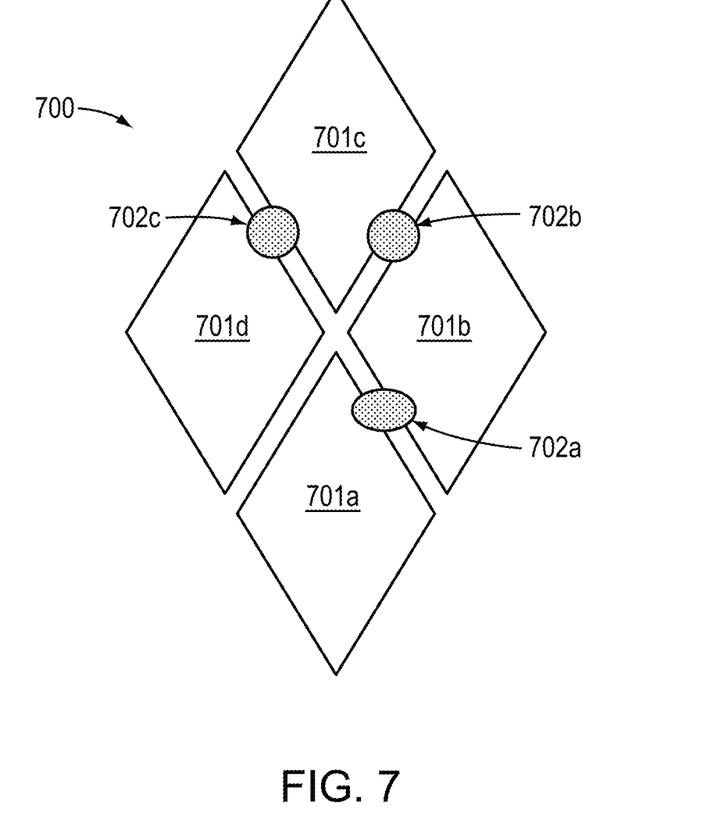
FIG. 7 is a schematic of a head probe system of four diamond head probe module, according to an embodiment of the invention.

FIG. 7 is a schematic of a head probe system of four diamond head probe modules. For certain regions of interest, a diamond shaped base with an optode layout matching that shown in FIG. 2a produces the optimal configuration with two light detectors and three light sources. Head probe system 700 is composed of head probe modules 701a, 701b, 701c, and 701d. One of head probe modules 701a, 701b, 701c, and 701d may be a master module. Head probe modules 701a, 701b, 701c, and 701d are connected at communication ports 702a, 702b, and 702c. The optodes located on head probe module 701a, 701b, 701c, and 701d can form channels with optodes located on their own base or with optodes located on any base of probe system 700.

Figure 8:
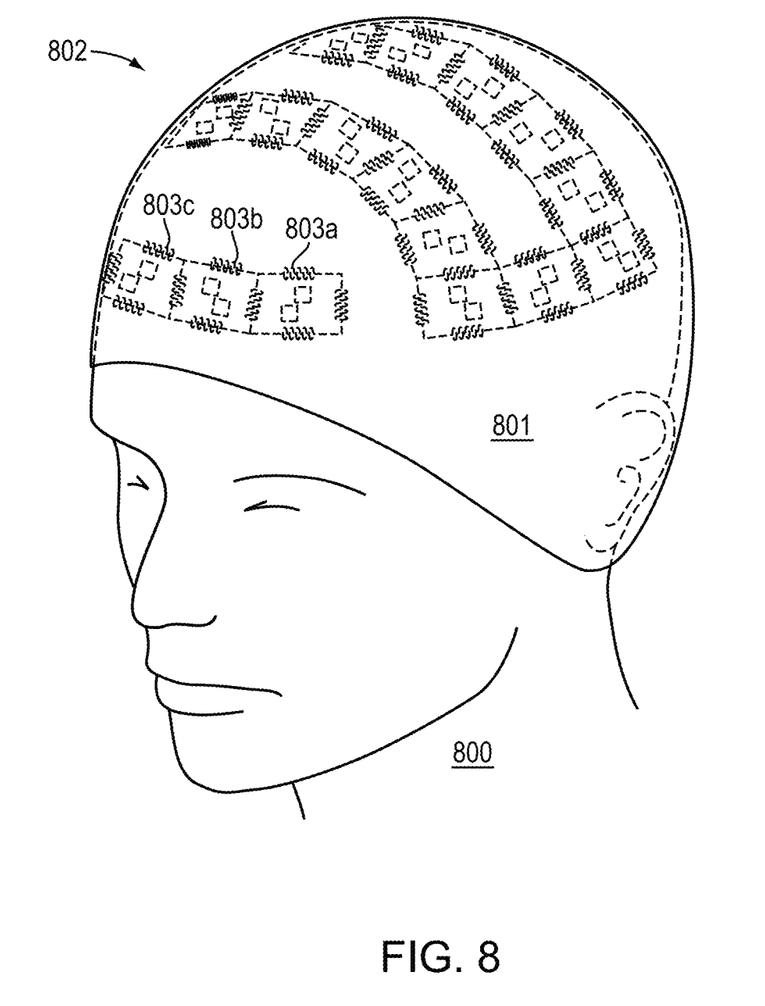
FIG. 8 is an illustration of a head probe system placed on a user's head, according to an embodiment of the invention.

FIG. 8 is an illustration of a head probe system placed on a user's head according to an embodiment of the invention. Head probe system 802 is comprised of head probe modules 803. In the example embodiment shown in FIG. 8, head probe modules 803 are square and connected in series. Head probe modules 803 may be the head probe modules 300a-e shown in FIG. 3. Head probe modules 803 may be cut and resoldered to be connected and reconnected in any desired configuration. The modular nature of head probe system 802 and head probe modules 803 allows for any desired region of the head of user 800 to be monitored. A user 800, can secure head probe 802 to their head using cap 801. Head probe system 802 may be connected to cap 801. Alternatively, head probe system may be loose against the head of user 800 and secured using tension from cap 801.

The integration of position sensors 208, and optodes 201 and 202 into a single modular circuit allows the head probe to provide positional and motion data for each individual channel (source-to-detector) measurement. This drastically reduces probe setup time by avoiding an additional measurement of all sources and detectors, but also increases accuracy by taking into account the source-detector distance deformation when placed on a 3D surface such as a user's head. The integration of position sensors 208, also help the formation of a head probe system from multiple head probe modules. The ability to automatically the position, and in some embodiments the orientation, of each source and detector in a head probe system, allows the system to automatically make use of cross-module channels (source-detector pairs from different head probe modules), increasing channel density over a region of interest without a user's input or additional activity such as external position measurements. This is not possible in prior art fNIRS designs.

The position and motion data from the position sensors also permits the mapping of fNIRS data from the optodes onto a tomographic reconstruction of the user's head and allows for the consideration of accurate brain anatomical structures. This 3D tomographic analysis provides increased accuracy in measuring and deriving brain activity. The position and motion data from the position sensors also allow for the ability to recover the location and spatial arrangements of the light detectors and light sources.

Furthermore, position and optical data are captured simultaneously in real-time. This allows the ability to detect and correct for motions in the system during physical movement and track channel distance while in use, rather than calibrating once prior to use, ensuring data during long-term use is accurate. The motion and positioning data provided by position sensors 208, allows for both the simultaneous per-channel motion recording to help detect and correct motion artifacts and enable real-time motion-artifact detection, correction and data pruning using position sensor data. This may include identifying and excluding data from an optode pair that shifted too much or correcting the gathered data based on a new channel distance. Real-time and simultaneous sensor data also informs data quality, allowing for data cleaning and processing that corrects for and removes data artifacts. Continuous mapping of physiological measurements improves the accuracy of data captured during long-term monitoring in natural environments and other non-laboratory conditions.

The invention may also allow characterizing biological tissues using simultaneous position and physiological data enabled by integrated position sensors 208. Position sensors, 208, can measure the shape of the user's head, creating 3D surfaces to make 3D tomographic analysis possible, resulting in high accuracy in brain activities. Physiological measurements derived from optodes 201 and 202 can be mapped to volumetric images created from the position data from position sensors using signal processing reconstruction techniques. This automatic mapping allows for a reduction in setup time, reduces operator variability, and reduces the number of external components needed in a system.

The invention includes a computational model-driven, structural-prior-guided, tomographic brain functional image reconstruction pipeline. Robust signal processing methods can be applied to further suppress motion artifacts; cortically constrained diffuse optical tomography (DOT) reconstruction algorithms, in combination with "speculative priors," can be performed to obtain 3D localized dynamic brain activation maps that use both channel data from optodes 201 and 202 and motion and positioning data from position sensors 208.

The raw data from the individual source/detector channels from optode 201 and 202 can be preprocessed to remove the physiological contamination from the superficial layer 104 and suppress motion artifacts. An example of data preprocessing can be found in [Huppert2017] Barker J, B Schmidt, S Walls, and A Ghuman, "Comparison of group-level, source localized activity for simultaneous functional near-infrared spectroscopy-magnetoencephalography and simultaneous fNIRS-fMRI during parametric median nerve stimulation," Neurophotonics, vol. 4, no. 1, p. 15001, 2017 which is incorporated by reference. The raw optical signals, in one embodiment recorded at around 10 Hz per channel, are first calibrated and converted to optical density, in one embodiment this is done at both 690 and 830 nm. The raw optical signals can then be analyzed using a statistical general linear model (GLM). An iterative estimation of an autoregressive ("AR") whitening filter and weighted-least-squares (WLS) regression can both be applied to reduce the effects of serially correlated noise and motion artifacts in the raw data. This may be done by first constructing a design matrix, X, from the convolution of a canonical hemodynamic response function (AFNI GAM function) with the stimulus onsets and durations of the median nerve stimulation events. A linear regression model is constructed of the form $Y=X \cdot \beta$, where Y is the vector of time-points for each optode pair and $\beta$ is the estimated weights of the regressors. The values of $\beta$ are first estimated from a weighted least-squares procedure (robustfit). A p-th order autoregressive model is then applied to fit the residual error of the regression fit. The order p is estimated by an Akaike information criterion (AIC) search. The autoregressive coefficients are used to construct a whitening filter (S-1), which is then applied to both the left and right-hand-sides of the regression model (e.g., $S\text{-}1 \cdot Y = S\text{-}1 \cdot X \cdot \beta$). The regression model is solved again using robust regression methods and the procedure is iterated until convergence. This is repeated for each optical measurement channel and wavelength. This procedure is robust in removing various forms of artifacts, especially large amplitude infrequent motion artifacts. This model can robustly remove superficial physiological contamination.

Once the raw data has undergone pre-processing the positional data can be incorporated. By processing the data from position sensors 208, for each head probe, relative orientations between neighboring head probes can be obtained and the 3D locations of all optodes on the user's head can be derived. First initialize the data from position sensors 208, in a 2D configuration on a flat surface; an initial head probe configuration will be recorded based on module connection topology and data from position sensor 208. The flexible circuit substrate forming base 200 connecting the modules may be modeled using splines with the measured normal directions from the corresponding module position sensor 208. The relative 3D positions of all modules can be estimated by iteratively calculating the curves connecting any two adjacent modules, since the curves are assumed to have known length equal to the geodesic distance between two position sensors 208. After the 3D reconstruction of optode positions, an Affine transform is can be used to scale the probe to match the distances between selected 10-20 landmarks (such as inion-to-nasion) obtained from the subject.

Two offline, DOT-based brain activation reconstruction workflows can be used to provide detailed spatial maps of brain activity using optical data and 3D optode positions. Alternatively, the reconstruction can be done by the master module. For subjects with a previously acquired structural MRI scan, subject-specific anatomical models can be used and run a cortically constrained Gauss-Newton reconstruction to recover the 3D brain activation maps. One embodiment uses, the MM scan (T1 or T1+T2 weighted) segmented using SPM, from which a voxelated brain segmentation or a tetrahedral mesh can be created. The optode positions provided by position sensor 208, can be registered to the scalp of the subject. In one embodiment this is done using "Metch" MATLAB toolbox. GPU-based Monte Carlo simulations with a photon-replay algorithm can be run to create the Jacobians corresponding to the source and detector pairs for a given cortical region-of-interest (or full head). For a given subject and region of interest, the Jacobian only needs to be computed once. It can then be applied to all time-points from the relevant optical channels to recover time-varying brain activity until an optode movement is detected. A GPU-based adaptive non-local-mean (ANLM) filter will be applied to the MC-derived Jacobians to reduce the stochastic noise, permitting rapid calculations using only a small number of photons.

For subjects whose MRI scans are not available (such as the healthy subjects), a developmental brain atlas library for 3D reconstruction can be used. First the brain atlas that matches the subject's age and is selected then the atlas is registered to the head probe positions (which characterizes the subject's scalp surface), and the MC-based DOT reconstruction is run as outlined above.

Some embodiments can incorporate a "speculative-prior-guided" reconstruction algorithm to significantly improve the contrast and resolution of the brain activation estimation. This includes defining a small Gaussian-sphere as the probability map of the activation and moving it in small steps across the cortical region-of-interest. The change in HbT before and after using the prior will be calculated and mapped to the speculated activation position. After scanning a region of interest, an enhanced activation map that is highly sensitive to small-localized HbT changes will be produced following each applied stimulus (or any given time point). If a single-interaction (i.e. linear) reconstruction is performed, no additional Monte Carlo calculation is needed because the Jacobians used in these reconstructions are the same as those in non-prior reconstructions. The only things that need to be re-evaluated between different speculated locations are the regularization matrix (L) and the solution of the normal equation.

While example embodiments have been particularly shown and described, it will be understood by those skilled in the art that various changes in form and details may be made therein without departing from the scope of the embodiments encompassed by the appended claims.

What is claimed is:

1. A head probe comprising:
plural flexible modules, each module comprising:
    a communication port configured to temporarily physically interface one of the plural modules with another of the plural modules to create an inter-connected system of modules;
    a flexible base configured to conform to a section of a user's head surface;
    a first light source, on a surface of the base facing the user's head, that propagates light through a user's head tissue;
    a first photodetector, on the surface of the flexible base facing the user's head, that detects light from the first light source after the light traverses the user's head tissue; and
    a position sensor that gathers positioning and motion data of the head probe, the positioning and motion data representative of locations and spatial arrangement of the first light source and the first photodetector.

2. The head probe of claim 1 wherein the position sensor includes a 3-axis accelerometer and a gyroscope.

3. The head probe of claim 1 wherein the light propagated is near-infrared light with a wavelength between 600-2500 nm.

4. The head probe of claim 1 wherein the first photodetector detects light on a first flexible module from a light source on an interfaced second flexible module after the light traverses the user's head tissue.

5. The head probe of claim 1 further comprising a wireless transceiver.

6. The head probe of claim 1 wherein the flexible base is diamond shaped, composed of two triangles connected along one edge.

7. The head probe of claim 1 wherein the plural flexible modules each further comprises a second photodetector, on the surface of the flexible base facing the user's head, located farther from the first light source than the first photodetector that detects the light from the first light source after the light traverses the user's head tissue.

8. The head probe of claim 7 wherein the plural flexible modules each further comprises:
    a second light source, on the surface of the flexible base facing the user's head, that propagates additional light through the user's head tissue; and
    wherein the first and the second photodetectors detect the light emitted by the first light source and the additional light emitted by the second light source after the light and the additional light traverse the user's head tissue.

9. A modular head probe system comprising:
plural flexible modules, each comprising:
    a communication port configured to temporarily interface with another of the plural modules to create an inter-connected system of modules;
    a light source, on a surface facing a user's head, that propagates light from the light source through a user's head tissue;
    a light detector, on the surface of the given module facing the user's head, that detects the light from the light source after the light traverses the user's head tissue; and
    a position sensor; and
a master module comprising a controller, the controller configured to determine physiological data of the user's head tissue based upon light detected by the photodetectors of the plural flexible modules, the controller further configured to use the motion and positioning data gathered by the position sensors of the plural flexible modules to recover locations and spatial arrangements of the light detectors and the light sources of the plural flexible modules.

10. The modular head probe system of claim 9 wherein the plural flexible modules and the control unit are configured to be connected, disconnected, and reconnected in multiple layout configurations.

11. The modular head probe system of claim 9 wherein the physiological data comprises hemodynamics.

12. The modular head probe system of claim 9 wherein the controller is further configured to use the locations and the spatial arrangements of the light detectors and the light sources of the plural flexible modules to perform at least one of the following: data cleaning, data processing, data correction, data pruning, and detection of data artifacts on the physiological data.

13. The modular head probe system of claim 9 wherein the plural modules are further configured to be connected using inter-integrated circuit protocol.

14. The modular head probe system of claim 9 wherein the master module includes a wireless transceiver and an external power source connection.

15. The modular head probe system of claim 9 wherein the physiological data is determine, and wherein the motion and positioning data is gathered in real time during user activity.

16. The modular head probe system of claim 9 further comprising a backend computer configured to determine all connection routes between the plural flexible modules and the master module and further configured to determine an optimized module layout.

17. The modular head probe system of claim 16 wherein the optimized module layout is defined as maximizing an average brain sensitivity.

18. The modular head probe system of claim 9 further comprising a computer configured to use the locations and the spatial arrangements of the light detectors and the light sources of the plural flexible modules to map the physiological data to a tomographic reconstruction of the user's head tissue.

* * * * *